US00PP14377P39

(12) United States Plant Patent
Whetman

(10) Patent No.: US PP14,377 P3
(45) Date of Patent: Dec. 16, 2003

(54) DIANTHUS PLANT NAMED 'DEVON SISKIN'

(50) Latin Name: *Dianthus x hydrida*
Varietal Denomination: Devon Siskin

(76) Inventor: John Whetman, Houndspool Ashcombe Rd., Dawlish Devon EX30QP (GB)

( * ) Notice: Subject to any disclaimer, the term of this patent is extended or adjusted under 35 U.S.C. 154(b) by 62 days.

(21) Appl. No.: 10/072,112

(22) Filed: Feb. 7, 2002

(65) Prior Publication Data

US 2003/0150034 P1 Aug. 7, 2003

(51) Int. Cl.[7] ..... A01H 5/00
(52) U.S. Cl. ..... Plt./272

(58) Field of Search ..... Plt./272, 273, 278, Plt./282, 283

(56) References Cited

PUBLICATIONS

The New Royal Horticultural Society Dictionary of Gardening, vol. 2, Editor–in–Chief Anthony Huxley, The Stockton Press, New York, 1992, pp. 50–56.*

* cited by examiner

*Primary Examiner*—Anne Marie Grunberg

(57) ABSTRACT

A new cultivar of Dianthus named 'Devon Siskin' that is characterized by fragrant red-purple flowers with a distinctive pattern, a compact mounding habit and a long flowering season. In combination the traits set 'Devon Siskin' apart from all other existing varieties of Dianthus known to the inventor.

2 Drawing Sheets

Genus: Dianthus.
Species: ×hybrida.
Denomination: Devon Siskin.

BACKGROUND OF THE INVENTION

The present invention relates to anew and distinct dwarf variety of Carnation that is grown for its compact habit, long flowering and distinctive flower pattern. The new cultivar is known botanically as Dianthus×hybrida and will be referred to hereinafter by the cultivar name 'Devon Siskin'.

'Devon Siskin' is the product of a breeding program conducted by the inventor in a cultivated area of Houndspool, Dawlish, Devon, United Kingdom. The primary focus of the breeding program was to produce varieties exhibiting a compact growth habit, new flower color forms and a long flowering season. The breeding program was established in 1985 in a cultivated area of Houndspool, Dawlish, Devon, United Kingdom, 'Devon Siskin', is an open pollinated seedling resulting from over 100 seedlings from the variety Dianthus 'Kessock Delight' (unpatented).

'Devon Siskin' is a hybrid produced by induced hybridization and was selected by the inventor in 1997 for its distinctive flowering pattern, compact habit and long flowering season. The male parent is an unidentified Dianthus and the female parent is Dianthus 'Kessock Delight' (unpatented). 'Devon Siskin' is distinguishable from the female parent plant by flower color, shorter sterns, unique flower pattern, more compact habit, larger flower, and free flowering. In comparison, the plant most similar to 'Devon Siskin' also Dianthus 'Kessock Delight'. The flower of 'Kessock Delight' is a solid purple color (83C) and is 2 cm. in diameter, whereas the flower petals of 'Devon Siskin' are made up of five colors that include white, pink and shades of reddish purple, and the flower measures 3.75 cm. in diameter.

Asexual reproduction of the new cultivar was first accomplished in 1998 by the inventor using softwood shoot cuttings in a cultivated area of Houndspool, Dawlish, Devon, United Kingdom. Since that time the characteristics of the new cultivar have been determined stable and are reproduced true to type in successive generations.

SUMMARY OF THE INVENTION

The following traits have been repeatedly observed and represent the characteristics of the new cultivar 'Devon Siskin'. These traits in combination distinguish this cultivar from all other commercial varieties known to the inventor. 'Devon Siskin' has not been tested under all possible conditions and phenotypic differences may be observed with variations in environmental, climatic and cultural conditions.

1. Dianthus 'Devon Siskin' exhibits a loose cushion or mounding growth habit.
2. Dianthus 'Devon Siskin' exhibits a distinctive flower pattern.
3. Dianthus 'Devon Siskin' exhibits free flowering fragrant flowers with colors that include white, pink, and purple on an individual flower.
4. Dianthus 'Devon Siskin' reaches 25 cm. in height including flower stalks and 20 cm. in width at maturity.
5. The lastingness of an individual 'Devon Siskin' flower is 5–10 days.
6. Dianthus 'Devon Siskin' is long flowering, blooming from April to October.
7. Dianthus 'Devon Siskin' is hardy to minus 15° Centigrade.

BRIEF DESCRIPTION OF THE DRAWINGS

The accompanying color drawings illustrate the overall appearance of the new cultivar 'Devon Siskin' showing the colors as true as it is reasonably possible to obtain in colored reproductions of this type. Colors in the photograph may differ from the color values cited in the detailed botanical description, which more accurately describe the actual colors of the new variety 'Devon Siskin'.

The drawing on sheet 1 illustrates the foliage, bud and flowers on a mature plant.

The drawing on sheet 2 is a close-up view of the flower. Both drawings are photographs taken of plants in Houndspool, Dawlish, Devon, United Kingdom in October 2001. No chemicals were used in treating the illustrated plants. Both drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Siskin'. Data was collected from mature plants in the United Kingdom. The color determinations are in accordance with The 1995 Royal Horticultural Society Colour Chart of The Royal Horticultural Society, London, England, except where general color terms of ordinary dictionary significance are used.

Botanical classification: Dianthus 'Devon Siskin'. Species: ×hybrida.

Commercial classification: Herbaceous perennial.

Use: Container and landscape plant.

Parentage: 'Devon Siskin' is a hybrid that resulted from the induced hybridization of the following parent plants:

- *Female parent.*—Dianthus 'Kessock Delight' (unpatented).
- *Male parent.*—Unidentified Dianthus.

Plant description:

- *Bloom period.*—April to October.
- *Plant habit.*—Plants form a loose cushion or mound.
- *Sexuality.*—Dioecious.
- *Height.*—25 cm. in height (including flower stalks).
- *Width.*—20 cm. in width.
- *Hardiness.*—Hardy to minus 15° Centigrade.
- *Vigor.*—Vigorous. 200% of a dwarf Dianthus.
- *Type.*—Perennial herb.
- *Root system.*—Fine, fibrous, deep rooting system.
- *Propagation.*—Propagation is accomplished with softwood shoot cuttings.
- *Cultural requirements.*—Plant in full sun and well drained loam or sandy loam of good physical structure with a pH of 6.5–7.0. This variety needs a high light intensity and long days.
- *Diseases and pests.*—Susceptible to known Dianthus pests and disease but no other susceptibilities are known to the inventor.
- *Time required to produce roots.*—2–3 weeks is needed to produce roots on initial cutting.
- *Temperature recommended for cuttings to produce roots.*—The air temperature required is 15–18° Centigrade and the base heat required is 21° Centigrade.
- *Crop time.*—3–5 months in needed for a rooted cutting to reach a finished one-liter liter container size.

Stem:

- *Shape.*—Cylindrical.
- *Basal stem dimensions.*—10 cm. in length and 0.25 cm. in diameter.
- *Stem surface.*—Glabrous and waxy.
- *Stem color.*—189B.
- *Branching.*—Numerous basal breaks.
- *Internode length.*—4–5 cm. between nodes.
- *Node color.*—160D.
- *Node dimensions.*—0.50 cm. in diameter and 0.50 cm. in height.

Foliage:

- *Type.*—Evergreen.
- *Shape.*—Lanceolate.
- *Division.*—Simple.
- *Apex.*—Acuminate.
- *Base.*—Concave.
- *Venation pattern.*—Parallel but not visible to the naked eye.
- *Vein color* (*abaxial surface*).—133C.
- *Vein color* (*adaxial surface*).—133B.
- *Margins.*—Entire.
- *Attachment.*—Sessile.
- *Stipules.*—None.
- *Petiole.*—None.
- *Arrangement.*—Opposite.
- *Surface* (*adaxial and abaxial*).—Glabrous and waxy.
- *Leaf dimensions.*—70 mm. in length and 4 mm. in width.
- *Leaf color* (*adaxial surface*).—133B.
- *Leaf color* (*abaxial surface*).—133C.
- *Fragrance.*—None.

Flowers:

- *Type.*—Raceme.
- *Persistent or self-cleaning.*—Persistent.
- *Flower dimensions.*—30 mm. in height (including the calyx, corolla and petals) and 40 mm. in diameter.
- *Flower shape.*—Disc shaped with tube below.
- *Throat depth.*—20 mm. in depth.
- *Aspect.*—Facing upward.
- *Bud color.*—132C.
- *Bud dimensions.*—15 mm. in height and 5 mm. in diameter.
- *Bud shape.*—Cylindrical and with a bluntly pointed apex.
- *Petals.*—5 in number.
- *Petals fused or unfused.*—Unfused.
- *Petal margin.*—Irregular.
- *Petal shape.*—Fan shaped.
- *Petal color.*—Each petal is made up of five colors. The margin of each petal is closest to 71A, the widest light pink surface of each petal is 74D mixed with a paler pink 69D, the darkest reddish band is 59A, and the base of each petal near the throat is white 155D.
- *Corolla tube color* (*outside and inside*).—155A.
- *Petal surface.*—Fluted.
- *Calyx dimensions.*—6 mm. in width and 20 mm. in length.
- *Calyx color.*—133B.
- *Calyx surface.*—Glabrous with distinct parallel veins.
- *Epicalyx* (*2 bracts basally fuse*).—133B.
- *Number of sepals.*—5 in number.
- *Sepals fused or unfused.*—Fused.
- *Sepal shape.*—Tubular.
- *Sepal margins.*—Minutely toothed.
- *Sepal apex.*—Acuminate.
- *Peduncle dimensions.*—25 cm. in length and 3 mm. in width.
- *Peduncle color.*—133C.
- *Peduncle surface.*—Glaucous and waxy.
- *Fragrance.*—Subtle clove scent.

*Lastingness of flower.*—An individual flower lasts 5–10 days on the plant.

Reproductive organs:

*Stamens.*—10 in number.

*Stamen dimensions.*—30 mm. in length and 1 mm. in diameter.

*Stamen color.*—155A.

*Anther color.*—The anther is a combination of 75C and 75D. It is the color 75C from the middle to the tip and the color 75D at the base of the anther.

*Anther shape.*—Sagitate.

*Pollen color.*—75D.

*Amount of pollen.*—Large amount.

*Anther dimensions.*—3 mm. in length and 1 mm. in diameter.

*Pistil.*—2.

*Pistil color.*—155A.

*Pistil dimensions.*—2 cm. in length and 1 mm. in diameter.

*Pistil shape.*—Fibril.

*Stigma.*—Single.

*Stigma color.*—155A.

*Style color.*—155A.

*Stigma dimensions.*—1 mm. in width and 30 mm. in length.

*Ovary position.*—Superior.

*Ovary color.*—150C.

*Ovary shape.*—Oval.

*Ovary dimensions.*—10 mm. in height and 4 mm. in width.

Seed production:

*Seed number.*—1–10 seeds produced.

*Seed shape.*—Flattened oval.

*Seed surface.*—Crinkled surface.

*Seed color.*—202A.

*Seed dimensions.*—1 mm. in diameter and 3 mm. in length.

*Fruit shape.*—Short stalked capsule.

*Fruit color.*—150D.

*Fruit size.*—11 mm. in height and 5 mm. in width.

I claim:

1. A new and distinct cultivar of Dianthus plant named 'Devon Siskin', as described and illustrated herein.

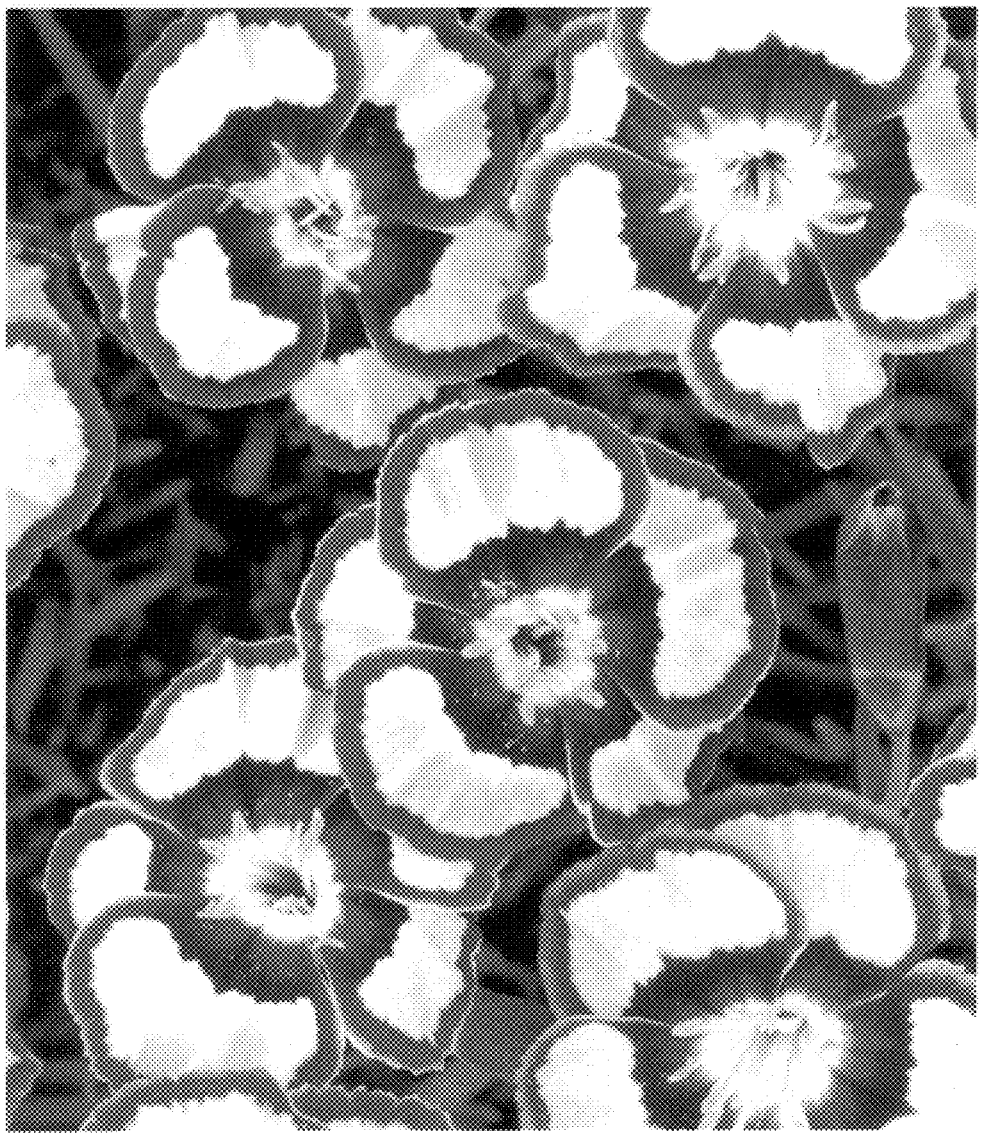

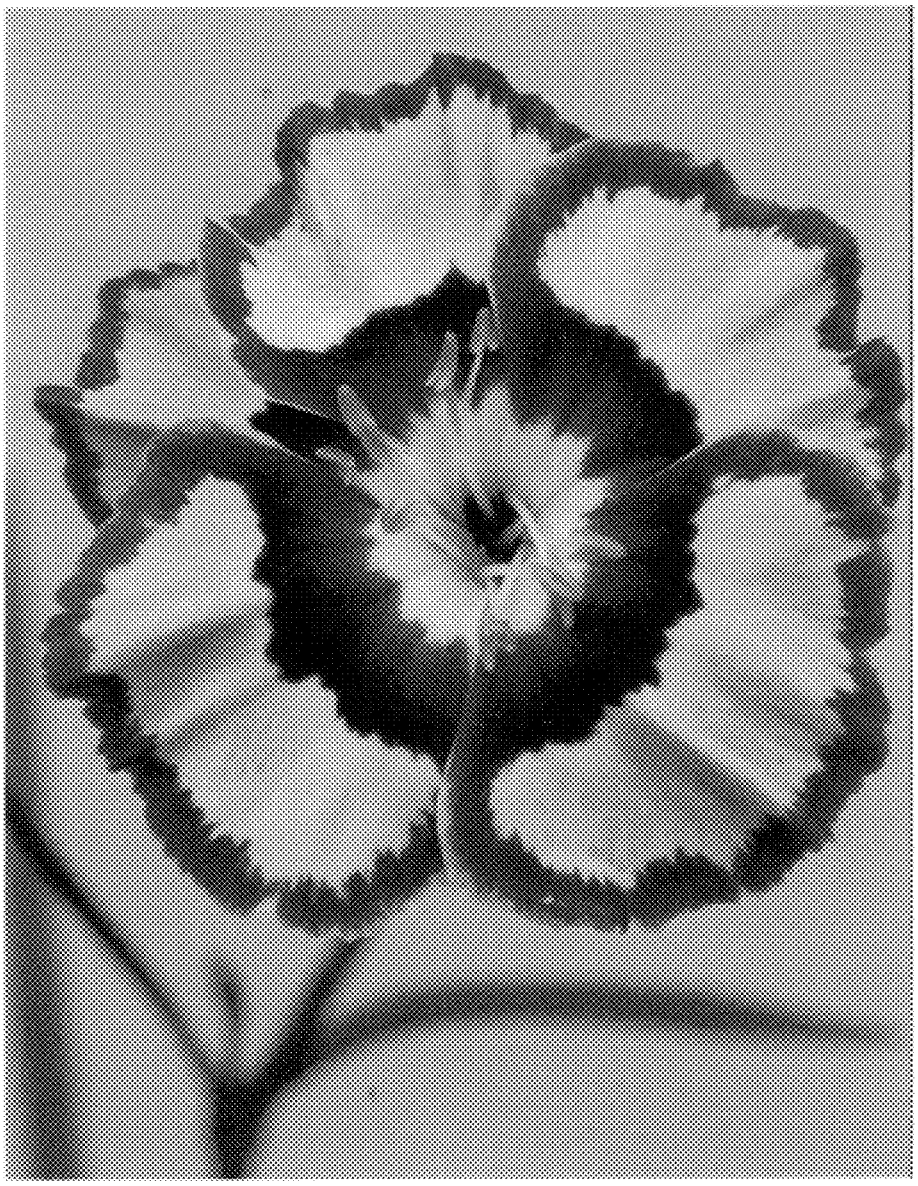

* * * * *